US012544207B2

(12) United States Patent
Svestka

(10) Patent No.: US 12,544,207 B2
(45) Date of Patent: Feb. 10, 2026

(54) FULL COVERAGE ABDOMINAL ANATOMIC HERNIA MESH

(71) Applicant: Michael Grant Svestka, Great Falls, VA (US)

(72) Inventor: Michael Grant Svestka, Great Falls, VA (US)

( * ) Notice: Subject to any disclaimer, the term of this patent is extended or adjusted under 35 U.S.C. 154(b) by 142 days.

(21) Appl. No.: 18/747,220

(22) Filed: Jun. 18, 2024

(65) Prior Publication Data

US 2024/0335273 A1 Oct. 10, 2024

Related U.S. Application Data

(63) Continuation-in-part of application No. 18/403,540, filed on Jan. 3, 2024, now Pat. No. 12,427,008.

(60) Provisional application No. 63/486,852, filed on Feb. 24, 2023.

(51) Int. Cl.
*A61F 2/00* (2006.01)

(52) U.S. Cl.
CPC .................................. *A61F 2/0063* (2013.01)

(58) Field of Classification Search
CPC ............ A61F 2002/0068; A61F 2/0077; A61F 2/0063; A61F 2/0045; A61F 2230/0045
See application file for complete search history.

(56) References Cited

U.S. PATENT DOCUMENTS

| | | | | |
|---|---|---|---|---|
| 5,840,011 | A * | 11/1998 | Landgrebe | A61F 2/0045 600/29 |
| 8,911,348 | B2 * | 12/2014 | Goldberg | A61F 2/0045 600/37 |
| 9,814,555 | B2 * | 11/2017 | Nagale | A61F 2/0045 |
| 10,813,743 | B2 * | 10/2020 | Spiegel | A61F 2/0059 |
| 11,045,579 | B2 * | 6/2021 | Barere | A61L 27/56 |
| 2008/0113001 | A1 * | 5/2008 | Herweck | A61L 31/14 424/445 |
| 2009/0187197 | A1 * | 7/2009 | Roeber | D04B 21/12 606/151 |
| 2010/0152530 | A1 * | 6/2010 | Timmer | B32B 5/26 600/37 |
| 2013/0211191 | A1 * | 8/2013 | Beyer | A61F 2/0045 600/37 |

* cited by examiner

*Primary Examiner* — Mohamed G Gabr

(57) ABSTRACT

A full coverage abdominal anatomic hernia mesh is a device that provides full coverage of the abdominal wall for abdominal wall reconstruction procedures. The device includes a mesh body with an upper mesh section, a lower mesh section, a lateral edge, and a primary horizontal axis. The mesh body is anatomically structured to provide coverage to the midline and lateral abdominal regions of the abdominal wall as well as to the groin region. The upper mesh section provides coverage to the midline and lateral abdominal regions. The lower mesh section provides coverage to the groin region. The upper mesh section has a larger surface area than the lower mesh section to cover a wider area of the abdominal wall. The lateral edge delineates the perimeter of the mesh body. The primary horizontal axis divides the mesh body into the upper mesh section and the lower mesh section.

20 Claims, 5 Drawing Sheets

FULL COVERAGE ABDOMINAL ANATOMIC HERNIA MESH

FIELD OF THE INVENTION

The present invention generally relates to hernia repair equipment. More specifically, the present invention discloses an individual prosthetic mesh that is anatomically configured to provide reinforcement to entire abdominal wall with additional pelvic coverage during abdominal wall reconstruction with the intention of treating all abdominal wall hernias.

BACKGROUND OF THE INVENTION

A hernia is characterized by a defect in the abdominal wall through which an organ, intestine, or fatty tissue can protrude. Hernias are often caused by a combination of tissue weakness, trauma, or prior incisions, and pose medical risk in that intestines can become trapped or incarcerated in these defects and lead to bowel compromise or death. According to the U.S. Food & Drug Administration, more than one million hernia repairs are performed each year in the U.S. Landmark studies from 2000 and 2004 demonstrated that the use of mesh prevents the risk of hernia recurrence by more than two times, and thus has become the standard of care. A hernia mesh is a type of medical prosthetic typically made from synthetic or biologic materials and is used to strengthen the hernia repair and reduce the rate of recurrence. The use of hernia mesh for prosthetic reinforcement of abdominal hernia defects has been a well-established practice for over 50 years. Commercially available mesh products are typically manufactured using polypropylene, polyester, or ePTFE polymers and are available in several sizes ranging from 2-3 centimeters (cm) to 50 by 50 cm sheets.

In general, hernia repair is approached in a stepwise fashion whereby the extent of the repair is dictated by the size of the hernia. In other words, smaller hernias require smaller mesh products while larger hernias require larger meshes. While smaller hernia defects are amenable to local repairs, as these defects recur and enlarge, reconstructive techniques utilizing muscle flaps developed out of abdominal wall tissue planes are required. Abdominal wall reconstruction is a category of hernia repair that encompasses a variety of surgical techniques used to fully reconstruct the abdominal wall and is indicated for very large hernia defects, or circumstances where numerous or recurrent hernia defects require definitive repair.

On the other hand, for large hernia defects, reconstructive techniques called "component separations" are used to separate the layers of the abdominal wall musculature. One such technique, known as transversus abdominis release, allows for coverage of the entire peritoneal cavity with reinforcing mesh. The tissue planes between muscle and fascia are developed and bilateral myofascial flaps are advanced towards the midline to close the visceral space. This allows for an extraperitoneal mesh to be placed between myofascial layers for reinforcement, placing the mesh outside of the peritoneal cavity (organ space) and between the abdominal wall muscles. These techniques of abdominal wall reconstruction generally use large sheets of mesh to reinforce midline, off-midline, and lateral hernia defects of the abdominal wall.

During abdominal wall reconstruction, the myofascial advancement flaps extend from the xiphoid to the pubic symphysis in the craniocaudal dimension, and bilaterally towards the retroperitoneum. Currently available mesh products do not encompass the full breadth of dissection during this procedure and fail to support the entirety of the abdominal wall. For example, available commercial mesh configurations allow for large sheets of diamond-shaped mesh to be placed in the cavity for reinforcement. These configurations, however, lack anatomic specificity and fail to reinforce the groin region where the localized hernia can be located. This is important as many patients undergoing abdominal wall reconstruction require additional coverage in the pelvic region.

Therefore, an objective of the present invention is to provide a solution to the aforementioned problems. The present invention discloses a single-mesh prosthetic that covers the full extent of the abdominal wall. The present invention is a total abdominal mesh which is anatomically configured to provide reinforcement to not only the midline and lateral abdomen, but also to the groin region during abdominal wall reconstruction. Additional features and benefits of the present invention are further discussed in the sections below.

SUMMARY OF THE INVENTION

The present invention discloses a full coverage abdominal anatomic hernia mesh designed to cover the full extent of the abdominal wall for abdominal wall reconstruction procedures. The present invention is anatomically configured to provide reinforcement to not only the midline and lateral abdomen, but also to the groin region. To do so, the present invention includes a single sheet of hernia mesh that is uniquely shaped to cover all regions described above. The upper mesh section of the hernia mesh is convex shaped with a pair of upper flaps that covers the abdominal region. Further, the lower mesh section of the hernia mesh corresponds to a pelvic protuberance that covers the groin region. Together, the upper mesh section and the lower mesh section provide full coverage of the abdominal wall during abdominal wall reconstruction.

DETAIL DESCRIPTIONS OF THE INVENTION

All illustrations of the drawings are for the purpose of describing selected versions of the present invention and are not intended to limit the scope of the present invention.

Figure 1:
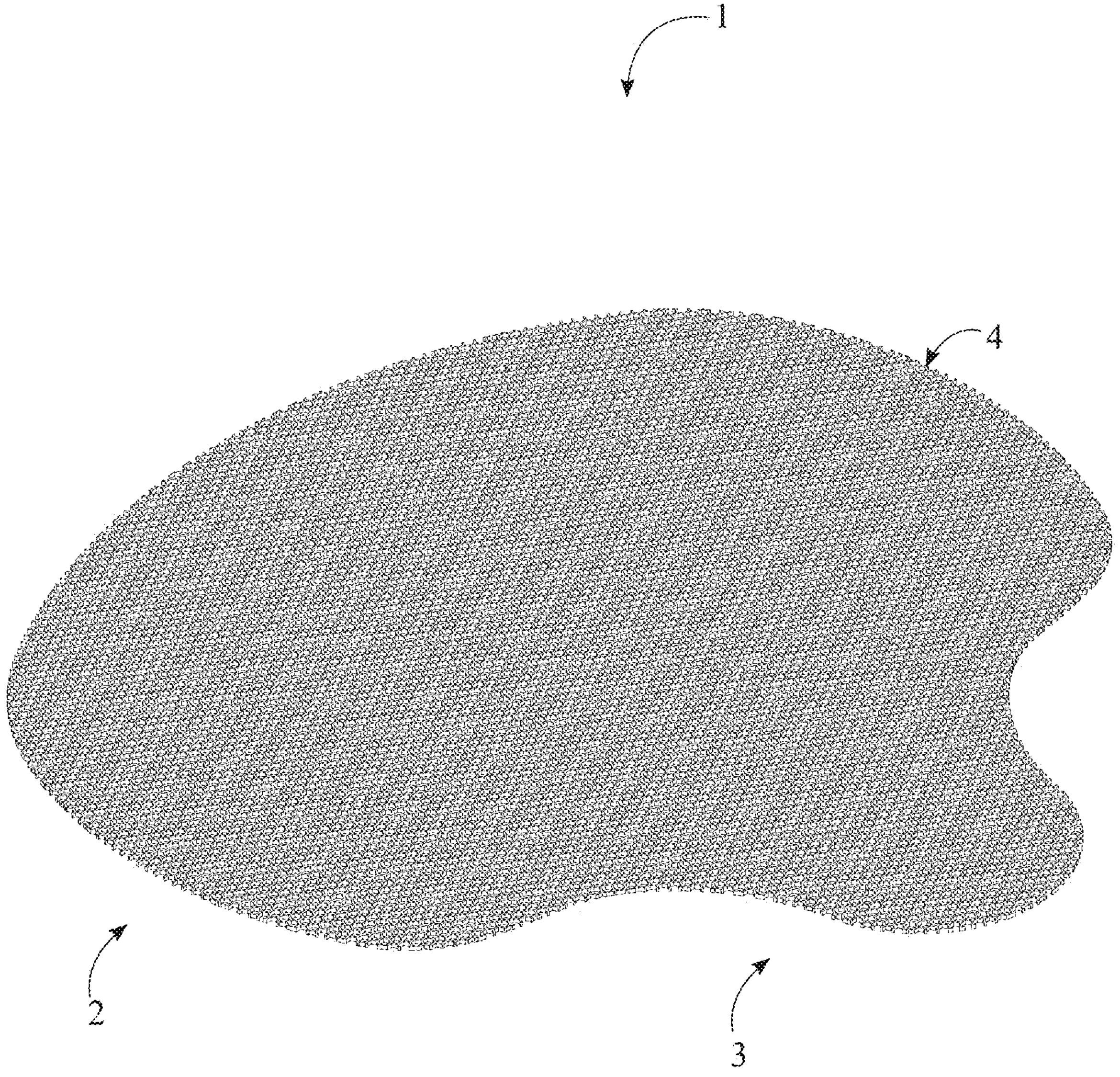
FIG. 1 is a perspective view of the mesh body of the present invention.
Figure 2:
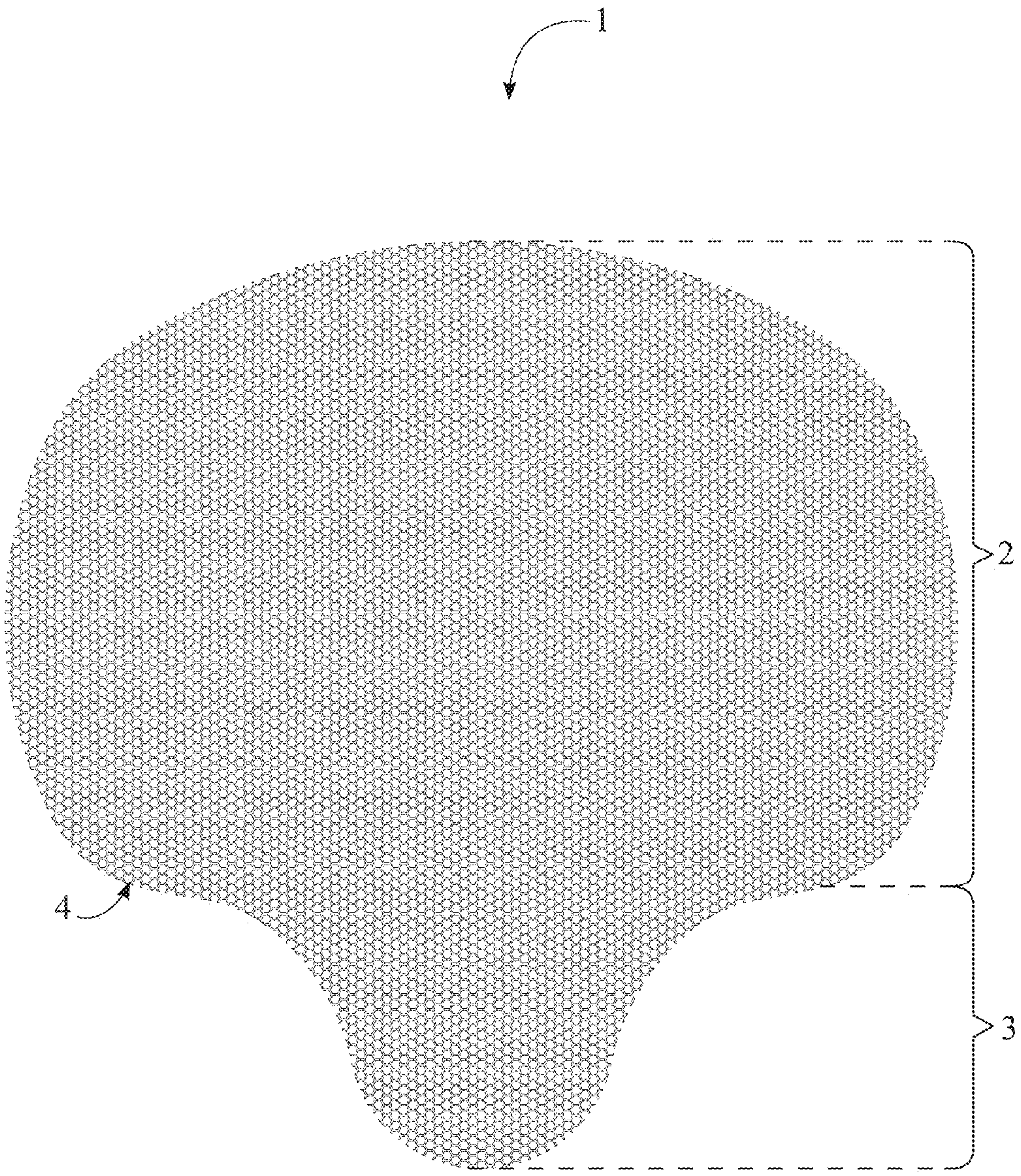
FIG. 2 is a front view of the mesh body of the present invention.
Figure 3:
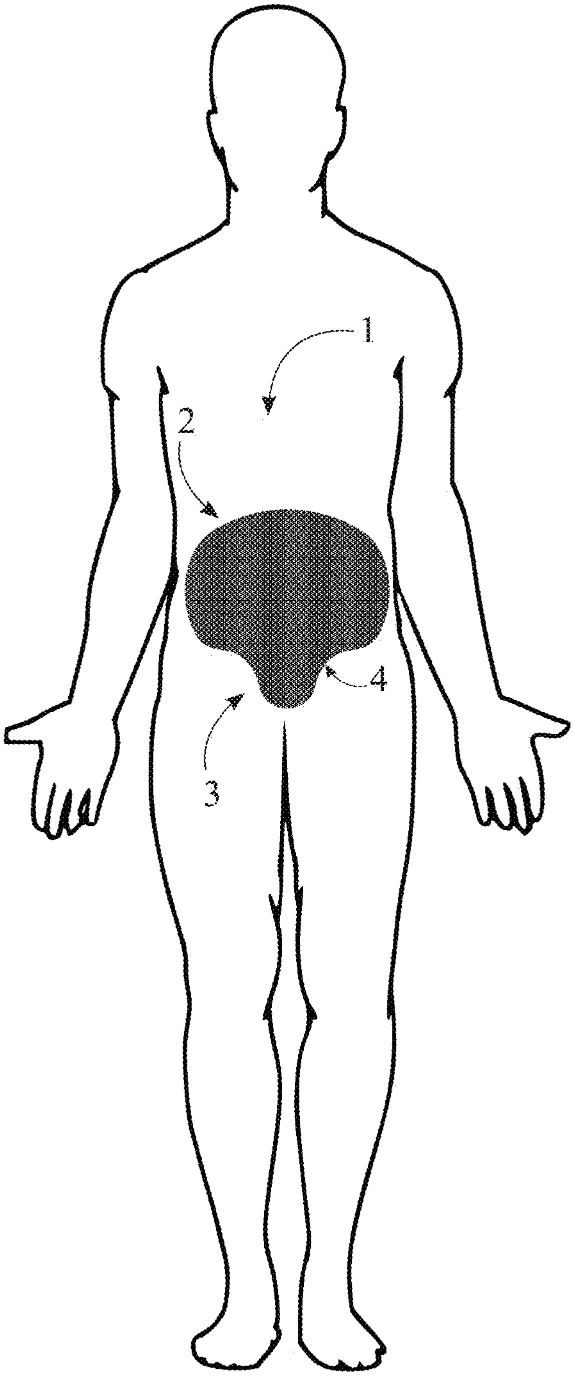
FIG. 3 is a front view of the mesh body of the present invention, showing the position of the mesh body in relation to a human body.

The present invention discloses a full coverage abdominal anatomic hernia mesh that provides reinforcement to the midline and lateral abdomen regions of the abdominal wall as well as the groin region for abdominal wall reconstruction procedures. As can be seen in FIG. 1 through 3, the present invention is preferably a singular prosthetic that is uniquely shaped to reinforce three types of hernia defects including midline, off-midline, and lateral hernias. Although the shape of the present invention is defined hereafter, the size of the present invention is not limited. In other words, the present invention can be produced in various sizes to accommodate the patient's anatomy. Similarly, the material of the present invention is not limited, and can be made of any type of medical-grade material based on design, user, manufacturing requirements, and/or medical requirements.

As can be seen in FIG. 1 through 3, the present invention comprises a mesh body 1 that is designed to provide full coverage of the abdominal wall. The mesh body 1 is anatomically structured to provide coverage to the midline and lateral abdominal regions of the abdominal wall as well as to the groin region. To do so, the mesh body 1 comprises an upper mesh section 2, a lower mesh section 3, a lateral edge 4, and a primary horizontal axis 15. The upper mesh section 2 is designed to provide coverage to the midline and lateral abdominal regions. On the other hand, the lower mesh section 3 is designed to provide coverage to the groin region. So, the upper mesh section 2 preferably has a larger surface area than the lower mesh section 3 to cover a wider area of the abdominal wall. In addition, the lateral edge 4 delineates the perimeter of the mesh body 1. Further, the primary horizontal axis 15 corresponds to the axis that divides the mesh body 1 into the upper mesh section 2 and the lower mesh section 3.

Figure 4:
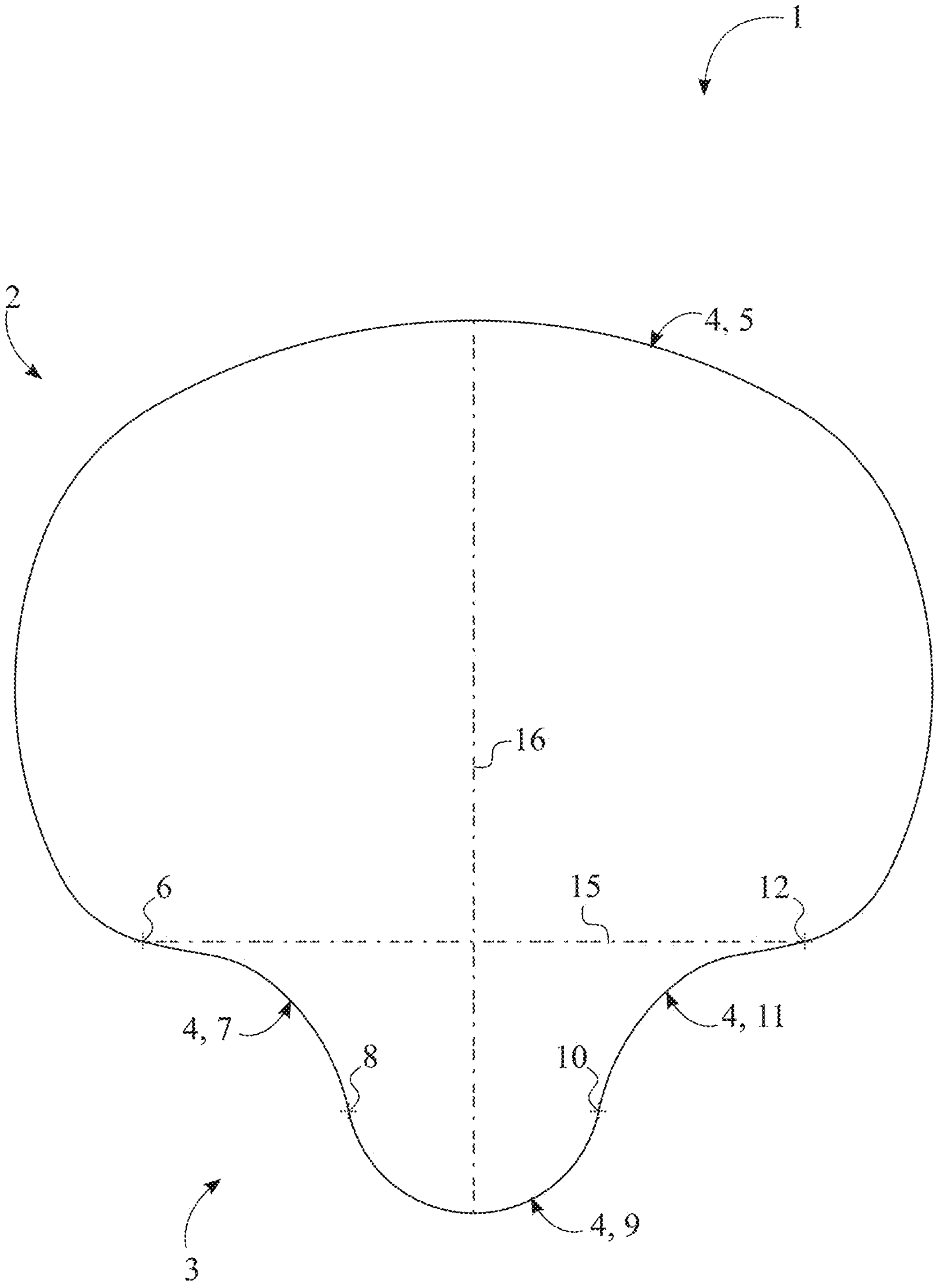
FIG. 4 is a schematic view of the mesh body of the present invention, wherein the mesh body is shown divided by a horizontal axis and a vertical axis, and wherein the axes are shown in dashed lines.

Furthermore, due to the anatomically structured shape of the mesh body 1, the lateral edge 4 comprises an upper convex edge section 5, a first inflection point 6, a first lower concave edge section 7, a second inflection point 8, a lower convex edge section 9, a third inflection point 10, a second lower concave edge section 11, and a fourth inflection point 12, as can be seen in FIG. 4. The upper convex edge section 5 preferably corresponds to the section of the lateral edge 4 surrounding the upper mesh section 2. The first lower concave edge section 7, the lower convex edge section 9, and the second lower concave edge section 11 correspond to the sections of the lateral edge 4 surrounding the lower mesh section 3. The first inflection point 6, the second inflection point 8, the third inflection point 10, and the fourth inflection point 12 corresponds to the points along the lateral edge 4 that delimit the different edge sections of the lateral edge 4.

The general configuration of the aforementioned components enables the full coverage of the abdominal wall using a single mesh structure. As can be seen in FIG. 1 through 4, the mesh body 1 is preferable made from a single piece of material to provide full coverage of the abdominal wall. In the preferred embodiment, the present invention can be arranged as follows: the upper mesh section 2 is positioned opposite to the lower mesh section 3 across the primary horizontal axis 15 due to the single mesh structure of the mesh body 1. Further, the lateral edge 4 is perimetrically positioned around the upper mesh section 2 and the lower mesh section 3 to define the outer perimeter of the mesh body 1. The upper mesh section 2 is anatomically shaped to reinforce the abdominal core (i.e., midline, off-midline, and lateral abdomen regions), while the lower mesh section 3 is anatomically shaped to reinforce the groin region. Thus, the overall shape of mesh body 1 covers the full extent of the abdominal wall to treat all hernia defects.

As previously discussed, the present invention eliminates the need of overlapping multiple hernia meshes that is currently conducted within the medical industry. The mesh body 1 is thus shaped to provide the necessary coverage with a single piece of mesh material. As can be seen in FIG. 4, the first inflection point 6 and the fourth inflection point 12 are positioned opposite to each other across the lower mesh section 3 due to the width of the lower mesh section 3. Likewise, the second inflection point 8 and the third inflection point 10 are positioned opposite to each other across the lower mesh section 3 due to the width of the lower mesh section 3. The first inflection point 6 and the fourth inflection point 12 preferably correspond to the edge points where the lateral edge 4 transitions from the upper mesh section 2 to the lower mesh section 3. Similarly, the second inflection point 8 and the third inflection point 10 preferably correspond to the edge points where the lateral edge 4 transitions from the lower convex edge section 9 to the first lower concave edge section 7 and the second lower concave edge section 11, respectively. Further, the upper convex edge section 5 extends from the first inflection point 6 to the fourth inflection point 12, adjacent to the upper mesh section 2. As a result, the upper mesh section 2 has a convex outer perimeter so that the upper mesh section 2 has an overall flat and round shape.

In addition, the first lower concave edge section 7 extends from the first inflection point 6 to the second inflection point 8, adjacent to the lower mesh section 3, as can be seen in FIG. 4. The first lower concave edge section 7 can be formed by performing a round lateral cut on the lower mesh section 3 to accommodate the natural shape of the pelvis. Further, on the opposite side of the lower mesh section 3, the second lower concave edge section 11 extends from the fourth inflection point 12 to the third inflection point 10, adjacent to the lower mesh section 3. Like the first lower concave edge section 7, the second lower concave edge section 11 can be formed by performing a round lateral cut on the opposite side of the lower mesh section 3 to accommodate the natural shape of the pelvis. Further, the lower convex edge section 9 is centered on the lower mesh section 3 to form a pelvic protuberance that provides coverage to the groin region. To do so, the lower convex edge section 9 extends from the second inflection point 8 to the third inflection point 10, adjacent to the lower mesh section 3. This way, the pelvic protuberance formed by the lower convex edge section 9 is rounded to provide coverage for the groin region.

As can be seen in FIG. 1 through 4, in the preferred embodiment, the mesh body 1 of the present invention is preferably a symmetrical structure that has vertical symmetry along a central vertical axis 16 of the mesh body 1. The symmetrical design of the mesh body 1 preferably matches the anatomy of the abdominal wall to provide full coverage without the need of additional mesh products. The central vertical axis 16 is preferably positioned perpendicular to the horizontal axis. In addition, the upper convex edge section 5, the upper mesh section 2, the primary horizontal axis 15, the lower mesh section 3, and the lower convex edge section 9 are bisected by the central vertical axis 16. This way, the mesh body 1 is vertically symmetric along the central vertical axis 16 to accommodate the anatomy of the abdominal wall.

Figure 5:
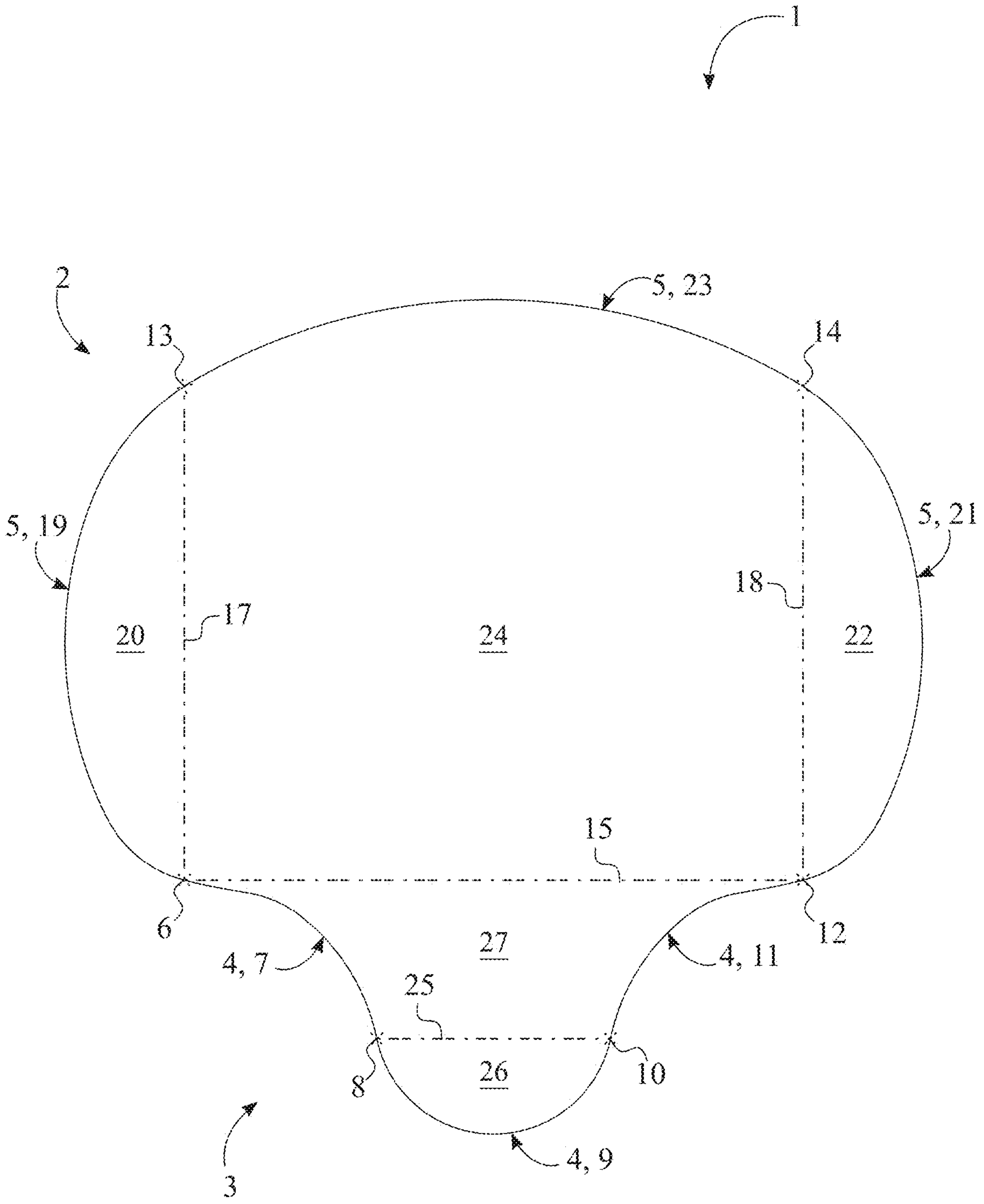
FIG. 5 is a schematic view of the mesh body of the present invention, wherein the mesh body is shown divided into body regions by horizontal axes and vertical axes, and wherein the axes are shown in dashed lines.

As previously discussed, the upper mesh section 2 is designed to cover the midline, off-midline, and lateral abdomen regions. As can be seen in FIG. 5, the mesh body 1 may further comprise a first vertical axis 17 and a second vertical axis 18 so that the upper mesh section 2 can be divided into three functional regions. In addition, the lateral edge 4 may further comprise a first intersection point 13 and a second intersection point 14 corresponding to the intersection points of the first vertical axis 17 and the second vertical axis 18 with the lateral edge 4, respectively. In the preferred embodiment, the first inflection point 6 and the fourth inflection point 12 are colinear with the primary horizontal axis 15. In other words, the primary horizontal axis 15 crosses the first inflection point 6 and the fourth inflection point 12 to position the primary horizontal axis 15 in between the upper mesh section 2 and the lower mesh section 3. Further, the first vertical axis 17 and the second vertical axis 18 are positioned parallel to each other. The first vertical axis 17 is also positioned perpendicular to the primary horizontal axis 15. This way, both the first vertical axis 17 and the second vertical axis 18 are perpendicular to the primary horizontal axis 15. Further, the first intersection point 13 and the second intersection point 14 are positioned along the upper convex edge section 5 so that the first vertical axis 17 and the second vertical axis 18 divide the upper mesh section 2. This way, the first inflection point 6 and the first intersection point 13 are colinear with the first vertical axis 17 so that the first vertical axis 17 crosses the first inflection point 6 and the first intersection point 13. Likewise, the fourth inflection point 12 and the second intersection point 14 are colinear with the second vertical axis 18 so that the second vertical axis 18 crosses the fourth inflection point 12 and the second intersection point 14. As a result, the first vertical axis 17 and the second vertical axis 18 divide the upper mesh section 2 into three regions.

In the preferred embodiment, the lateral region formed by the first vertical axis 17 on the upper mesh section 2 corresponds to a right flank region 20 of the mesh body 1. As can be seen in FIG. 5, the edge section surrounding the right flank region 20 also corresponds to a right subcostal margin 19 of the mesh body 1. The right subcostal margin 19 and the right flank region 20 are positioned on the upper mesh section 2 so that the mesh body 1 can extend over the abdominal wall and into the right rib cage to treat hernia repair and to prevent potential hernia spaces. So, the right subcostal margin 19 extends from the first inflection point 6 to the first intersection point 13 along the upper convex edge section 5. In addition, the right flank region 20 is delineated by the right subcostal margin 19 and the first vertical axis 17. As a result, the mesh body 1 can cover the abdominal wall region adjacent to the right rib cages.

As can be seen in FIG. 5, in a similar manner, the lateral region formed by the second vertical axis 18 on the upper mesh section 2 corresponds to a left flank region 22 of the mesh body 1. In addition, the edge section surrounding the left flank region 22 corresponds to a left subcostal margin 21 of the mesh body 1. The left subcostal margin 21 and left flank region 22 are positioned on the upper mesh section 2 so that the mesh body 1 can extend over the abdominal wall and into the left rib cage to treat hernia repair and to prevent potential hernia spaces. So, the left subcostal margin 21 extends from the fourth inflection point 12 to the second intersection point 14 along the upper convex edge section 5. In addition, the right flank region 20 is delineated by the left subcostal margin 21 and the second vertical axis 18. As a result, the mesh body 1 can cover the abdominal wall region adjacent to the left rib cage. Furthermore, due to the vertical symmetry of the mesh body 1, the right flank region 20 and the left flank region 22 preferably have equal surface areas.

As can be seen in FIG. 5, the first vertical axis 17 and the second vertical axis 18 divide the upper mesh section 2 into three regions. So, along with the right flank region 20 and the left flank region 22, a central abdomen region 24 is formed on the upper mesh section 2 that is positioned centrally on the upper mesh section 2. In addition, the edge section surrounding the central abdomen region 24 corresponds to an epigastric margin 23 of the mesh body 1. The epigastric margin 23 and the central abdomen region 24 are positioned within the upper mesh section 2 so that the mesh body 1 can extend over the abdominal wall to treat hernia repair and to prevent potential hernia spaces. So, the epigastric margin 23 extends from the first intersection point 13 to the second intersection point 14 along the upper convex edge section 5. In addition, the central abdomen region 24 is delineated by the first vertical axis 17, the epigastric margin 23, the second vertical axis 18, and the primary horizontal axis 15. As a result, the central abdomen region 24 is centered on the upper mesh section 2 with a surface area larger than the right flank region 20 and the left flank region 22. In other embodiments, different subregions can be formed on the upper mesh section 2 using different geometrical references.

As can be seen in FIG. 5, like the upper mesh section 2, the lower mesh section 3 can also be divided into subregions that provide coverage to different areas of the pelvis. For example, the mesh body 1 may further comprise a secondary horizontal axis 25 that horizontally divides the lower mesh section 3 into two subregions. The secondary horizontal axis 25 is positioned parallel and offset to the primary horizontal axis 15 to coincide with the position of the second inflection point 8 and the third inflection point 10. Further, the second inflection point 8 and the third inflection point 10 are colinear with the primary horizontal axis 15 so that the first lower concave edge section 7 and the second lower concave edge section 11 are symmetrical along the central vertical axis 16.

In the preferred embodiment, a first region formed by the secondary horizontal axis 25 corresponds to a pelvic space region 26 of the mesh body 1, as can be seen in FIG. 4. The pelvic space region 26 is formed on the lower mesh section 3 to provide coverage to the pelvic area of the abdominal wall. The pelvic space region 26 is delineated by the lower convex edge section 9 and the secondary horizontal axis 25 so that the pelvic space region 26 corresponds to the round protuberance of the lower mesh section 3. The pelvic space region 26 provides the necessary coverage in the groin region where a localized hernia can be positioned.

In addition to the pelvic space region 26, the mesh body 1 may further comprise a retzius space region 27 corresponding to the central region formed by the secondary horizontal axis 25, as can be seen in FIG. 4. The retzius space region 27 is positioned on the lower mesh section 3 so that the mesh body 1 can be positioned above the bladder and rest adjacent to the Cooper's ligament. So, the retzius space region 27 is delineated by the first lower concave edge section 7, the primary horizontal axis 15, the second lower concave edge section 11, and the secondary horizontal axis 25. This way, the retzius space region 27 is positioned in between the pelvic space region 26 and the central abdomen region 24 of the upper mesh section 2. In other embodiments, the lower mesh section 3 can be divided into different subregions according to different geometrical references.

Although the invention has been explained in relation to its preferred embodiment, it is to be understood that many other possible modifications and variations can be made without departing from the spirit and scope of the invention as hereinafter claimed.

What is claimed is:

1. A full coverage abdominal anatomic hernia mesh comprising:

a mesh body;

the mesh body comprising an upper mesh section, a lower mesh section, a lateral edge, and a primary horizontal axis;

the lateral edge comprising an upper convex edge section, a first inflection point, a first lower concave edge section, a second inflection point, a lower convex edge section, a third inflection point, a second lower concave edge section, and a fourth inflection point;

the upper mesh section being positioned opposite to the lower mesh section across the primary horizontal axis;

the lateral edge being perimetrically positioned around the upper mesh section and the lower mesh section;

the first inflection point and the fourth inflection point being positioned opposite to each other across the lower mesh section;

the second inflection point and the third inflection point being positioned opposite to each other across the lower mesh section;

the upper convex edge section extending from the first inflection point to the fourth inflection point, adjacent to the upper mesh section;

the first lower concave edge section extending from the first inflection point to the second inflection point, adjacent to the lower mesh section;

the second lower concave edge section extending from the fourth inflection point to the third inflection point, adjacent to the lower mesh section;

the lower convex edge section being centered on the lower mesh section; and the lower convex edge section extending from the second inflection point to the third inflection point, adjacent to the lower mesh section.

2. The full coverage abdominal anatomic hernia mesh as claimed in claim 1 comprising:

the mesh body further comprising a central vertical axis;

the central vertical axis being positioned perpendicular to the horizontal axis; and the upper convex edge section, the upper mesh section, the primary horizontal axis, the lower mesh section, and the lower convex edge section being bisected by the central vertical axis.

3. The full coverage abdominal anatomic hernia mesh as claimed in claim 1 comprising:

the mesh body further comprising a first vertical axis and a second vertical axis;

the lateral edge further comprising a first intersection point and a second intersection point;

the first inflection point and the fourth inflection point being colinear with the primary horizontal axis;

the first vertical axis and the second vertical axis being positioned parallel to each other;

the first vertical axis being positioned perpendicular to the primary horizontal axis;

the first intersection point and the second intersection point being positioned along the upper convex edge section;

the first inflection point and the first intersection point being colinear with the first vertical axis; and the fourth inflection point and the second intersection point being colinear with the second vertical axis.

4. The full coverage abdominal anatomic hernia mesh as claimed in claim 3 comprising:

the mesh body further comprising a right subcostal margin and a right flank region;

the right subcostal margin extending from the first inflection point to the first intersection point along the upper convex edge section; and the right flank region being delineated by the right subcostal margin and the first vertical axis.

5. The full coverage abdominal anatomic hernia mesh as claimed in claim 3 comprising:

the mesh body further comprising a left subcostal margin and a left flank region;

the left subcostal margin extending from the fourth inflection point to the second intersection point along the upper convex edge section; and the left flank region being delineated by the left subcostal margin and the second vertical axis.

6. The full coverage abdominal anatomic hernia mesh as claimed in claim 3 comprising:

the mesh body further comprising an epigastric margin and a central abdomen region;

the epigastric margin extending from the first intersection point to the second intersection point along the upper convex edge section; and the central abdomen region being delineated by the first vertical axis, the epigastric margin, the second vertical axis, and the primary horizontal axis.

7. The full coverage abdominal anatomic hernia mesh as claimed in claim 1 comprising:

the mesh body further comprising a secondary horizontal axis;

the secondary horizontal axis being positioned parallel and offset to the primary horizontal axis; and the second inflection point and the third inflection point being colinear with the primary horizontal axis.

8. The full coverage abdominal anatomic hernia mesh as claimed in claim 7 comprising:

the mesh body further comprising a pelvic space region; and the pelvic space region being delineated by the lower convex edge section and the secondary horizontal axis.

9. The full coverage abdominal anatomic hernia mesh as claimed in claim 7 comprising:

the mesh body further comprising a retzius space region; and the retzius space region being delineated by the first lower concave edge section, the primary horizontal axis, the second lower concave edge section, and the secondary horizontal axis.

10. A full coverage abdominal anatomic hernia mesh comprising:

a mesh body;

the mesh body comprising an upper mesh section, a lower mesh section, a lateral edge, a primary horizontal axis, a first vertical axis, and a second vertical axis;

the lateral edge comprising an upper convex edge section, a first inflection point, a first lower concave edge section, a second inflection point, a lower convex edge section, a third inflection point, a second lower concave edge section, a fourth inflection point, a first intersection point, and a second intersection point;

the upper mesh section being positioned opposite to the lower mesh section across the primary horizontal axis;

the lateral edge being perimetrically positioned around the upper mesh section and the lower mesh section;

the first inflection point and the fourth inflection point being positioned opposite to each other across the lower mesh section;

the second inflection point and the third inflection point being positioned opposite to each other across the lower mesh section;

the upper convex edge section extending from the first inflection point to the fourth inflection point, adjacent to the upper mesh section;

the first lower concave edge section extending from the first inflection point to the second inflection point, adjacent to the lower mesh section;

the second lower concave edge section extending from the fourth inflection point to the third inflection point, adjacent to the lower mesh section;

the lower convex edge section being centered on the lower mesh section;

the lower convex edge section extending from the second inflection point to the third inflection point, adjacent to the lower mesh section;

the first inflection point and the fourth inflection point being colinear with the primary horizontal axis;

the first vertical axis and the second vertical axis being positioned parallel to each other;

the first vertical axis being positioned perpendicular to the primary horizontal axis;

the first intersection point and the second intersection point being positioned along the upper convex edge section;

the first inflection point and the first intersection point being colinear with the first vertical axis; and the fourth inflection point and the second intersection point being colinear with the second vertical axis.

11. The full coverage abdominal anatomic hernia mesh as claimed in claim 10 comprising:

the mesh body further comprising a central vertical axis;

the central vertical axis being positioned perpendicular to the horizontal axis; and the upper convex edge section, the upper mesh section, the primary horizontal axis, the lower mesh section, and the lower convex edge section being bisected by the central vertical axis.

12. The full coverage abdominal anatomic hernia mesh as claimed in claim 10 comprising:

the mesh body further comprising a right subcostal margin and a right flank region;

the right subcostal margin extending from the first inflection point to the first intersection point along the upper convex edge section; and the right flank region being delineated by the right subcostal margin and the first vertical axis.

13. The full coverage abdominal anatomic hernia mesh as claimed in claim 10 comprising:

the mesh body further comprising a left subcostal margin and a left flank region;

the left subcostal margin extending from the fourth inflection point to the second intersection point along the upper convex edge section; and the left flank region being delineated by the left subcostal margin and the second vertical axis.

14. The full coverage abdominal anatomic hernia mesh as claimed in claim 10 comprising:

the mesh body further comprising an epigastric margin and a central abdomen region;

the epigastric margin extending from the first intersection point to the second intersection point along the upper convex edge section; and the central abdomen region being delineated by the first vertical axis, the epigastric margin, the second vertical axis, and the primary horizontal axis.

15. The full coverage abdominal anatomic hernia mesh as claimed in claim 10 comprising:

the mesh body further comprising a secondary horizontal axis, a pelvic space region, and a retzius space region;

the secondary horizontal axis being positioned parallel and offset to the primary horizontal axis;

the second inflection point and the third inflection point being colinear with the primary horizontal axis;

the pelvic space region being delineated by the lower convex edge section and the secondary horizontal axis; and the retzius space region being delineated by the first lower concave edge section, the primary horizontal axis, the second lower concave edge section, and the secondary horizontal axis.

16. A full coverage abdominal anatomic hernia mesh comprising:

a mesh body;

the mesh body comprising an upper mesh section, a lower mesh section, a lateral edge, a primary horizontal axis, a first vertical axis, a second vertical axis, and a central vertical axis;

the lateral edge comprising an upper convex edge section, a first inflection point, a first lower concave edge section, a second inflection point, a lower convex edge section, a third inflection point, a second lower concave edge section, a fourth inflection point, a first intersection point, and a second intersection point;

the upper mesh section being positioned opposite to the lower mesh section across the primary horizontal axis;

the lateral edge being perimetrically positioned around the upper mesh section and the lower mesh section;

the first inflection point and the fourth inflection point being positioned opposite to each other across the lower mesh section;

the second inflection point and the third inflection point being positioned opposite to each other across the lower mesh section;

the upper convex edge section extending from the first inflection point to the fourth inflection point, adjacent to the upper mesh section;

the first lower concave edge section extending from the first inflection point to the second inflection point, adjacent to the lower mesh section;

the second lower concave edge section extending from the fourth inflection point to the third inflection point, adjacent to the lower mesh section;

the lower convex edge section being centered on the lower mesh section;

the lower convex edge section extending from the second inflection point to the third inflection point, adjacent to the lower mesh section;

the first inflection point and the fourth inflection point being colinear with the primary horizontal axis;

the first vertical axis and the second vertical axis being positioned parallel to each other;

the first vertical axis being positioned perpendicular to the primary horizontal axis;

the first intersection point and the second intersection point being positioned along the upper convex edge section;

the first inflection point and the first intersection point being colinear with the first vertical axis;

the fourth inflection point and the second intersection point being colinear with the second vertical axis;

the central vertical axis being positioned perpendicular to the horizontal axis; and the upper convex edge section, the upper mesh section, the primary horizontal axis, the lower mesh section, and the lower convex edge section being bisected by the central vertical axis.

17. The full coverage abdominal anatomic hernia mesh as claimed in claim 16 comprising:

the mesh body further comprising a right subcostal margin and a right flank region;

the right subcostal margin extending from the first inflection point to the first intersection point along the upper convex edge section; and the right flank region being delineated by the right subcostal margin and the first vertical axis.

18. The full coverage abdominal anatomic hernia mesh as claimed in claim 16 comprising:

the mesh body further comprising a left subcostal margin and a left flank region;

the left subcostal margin extending from the fourth inflection point to the second intersection point along the upper convex edge section; and the left flank region being delineated by the left subcostal margin and the second vertical axis.

19. The full coverage abdominal anatomic hernia mesh as claimed in claim 16 comprising:

the mesh body further comprising an epigastric margin and a central abdomen region;

the epigastric margin extending from the first intersection point to the second intersection point along the upper convex edge section; and the central abdomen region being delineated by the first vertical axis, the epigastric margin, the second vertical axis, and the primary horizontal axis.

20. The full coverage abdominal anatomic hernia mesh as claimed in claim 16 comprising:

the mesh body further comprising a secondary horizontal axis, a pelvic space region, and a retzius space region;

the secondary horizontal axis being positioned parallel and offset to the primary horizontal axis;

the second inflection point and the third inflection point being colinear with the primary horizontal axis;

the pelvic space region being delineated by the lower convex edge section and the secondary horizontal axis; and the retzius space region being delineated by the first lower concave edge section, the primary horizontal axis, the second lower concave edge section, and the secondary horizontal axis.

* * * * *